US011589925B2

(12) United States Patent
Denissen et al.

(10) Patent No.: US 11,589,925 B2
(45) Date of Patent: Feb. 28, 2023

(54) MEDICAL SYSTEM USING OPTICAL SHAPE SENSING FIBER FOR TRIGGERING AN EVENT

(71) Applicant: KONINKLIJKE PHILIPS N.V., Eindhoven (NL)

(72) Inventors: Sander Hans Denissen, Best (NL); Wilhelmus Henrica Gerarda Maria Van Den Boomen, Valkenswaard (NL); Molly Lara Flexman, Melrose, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 417 days.

(21) Appl. No.: 15/755,314

(22) PCT Filed: Sep. 6, 2016

(86) PCT No.: PCT/EP2016/070913
§ 371 (c)(1),
(2) Date: Feb. 26, 2018

(87) PCT Pub. No.: WO2017/045963
PCT Pub. Date: Mar. 23, 2017

(65) Prior Publication Data
US 2018/0256261 A1    Sep. 13, 2018

Related U.S. Application Data

(60) Provisional application No. 62/219,151, filed on Sep. 16, 2015.

(30) Foreign Application Priority Data

Oct. 14, 2015    (EP) .................................... 15189813

(51) Int. Cl.
*A61B 34/20*    (2016.01)
*G06F 3/01*    (2006.01)
(Continued)

(52) U.S. Cl.
CPC .............. *A61B 34/20* (2016.02); *G06F 3/011* (2013.01); *A61B 6/12* (2013.01); *A61B 2017/00017* (2013.01); *A61B 2034/2061* (2016.02)

(58) Field of Classification Search
CPC ... A61B 34/20; A61B 6/12; A61B 2034/2061; A61B 2017/00017; G06F 3/011; G06F 3/01; G06F 3/017
See application file for complete search history.

(56) References Cited

U.S. PATENT DOCUMENTS 6,127,672 A  * 10/2000  Danisch ................. G01B 11/18
                                                  250/227.14
9,480,918 B2 * 11/2016  Hayashi ............... A63F 13/428
(Continued)

FOREIGN PATENT DOCUMENTS

WO    2013168055 A1    7/2013
WO    2013168056 A1    11/2013
WO    WO-2013168056 A1 *  11/2013    .............. G06F 3/011

*Primary Examiner* — Pascal M Bui Pho
*Assistant Examiner* — Adil Partap S Virk

(57) ABSTRACT

The present invention relates to a medical system using an interventional elongated medical device having an optical fiber configured for optical shape sensing of the medical device. The system comprises a detection unit configured to detect a confined manipulation section along the medical device for manipulation by a user without an interaction interface arranged on the medical device and an analysis unit configured to analyze a user manipulation applied to the manipulation section based on optical shape sensing of the medical device in the manipulation section and to trigger an event in the medical system, if the analysis unit identifies the (Continued)

user manipulation in the manipulation section as a specific manipulation associated with the event to be triggered.

20 Claims, 5 Drawing Sheets

(51) Int. Cl.
  *A61B 17/00* (2006.01)
  *A61B 6/12* (2006.01)

(56) References Cited

U.S. PATENT DOCUMENTS

| | | | |
|---|---|---|---|
| 2013/0150732 A1* | 6/2013 | Manzke | A61M 25/0082 600/478 |
| 2013/0310645 A1* | 11/2013 | Desjardins | A61B 1/0125 600/113 |
| 2014/0035798 A1 | 2/2014 | Kawada et al. | |
| 2014/0055345 A1* | 2/2014 | Seo | G06F 3/017 345/156 |
| 2014/0171964 A1* | 6/2014 | Yang | A61B 34/30 606/130 |
| 2014/0189560 A1 | 7/2014 | Caspi | |
| 2014/0357988 A1* | 12/2014 | Grass | G01T 1/161 600/424 |
| 2015/0045692 A1* | 2/2015 | Ramachandran | A61B 5/6852 600/549 |
| 2015/0109196 A1* | 4/2015 | Grass | G06F 3/014 345/156 |

* cited by examiner

MEDICAL SYSTEM USING OPTICAL SHAPE SENSING FIBER FOR TRIGGERING AN EVENT

CROSS-REFERENCE TO PRIOR APPLICATIONS

This application is the U.S. National Phase application under 35 U.S.C. § 371 of International Application Serial No. PCT/EP2016/070913, filed on Sep. 6, 2016, which claims the benefit of European Patent Application No. 15189813.7, filed on Oct. 14, 2015 and U.S. Patent Application No. 62/219,151, filed on Sep. 16, 2015. This application is hereby incorporated by reference herein.

FIELD OF THE INVENTION

The present invention relates to medical systems using an interventional elongated medical device equipped with an optical fiber configured for optical shape sensing of the medical device. In particular, the present invention relates to a medical system in which the optical shape sensing fiber can be used for triggering an event in the medical system.

BACKGROUND OF THE INVENTION

An operating theater usually has many user interfaces at the operating table side to control the system mechanics, imaging, visualization and other parts or sub-systems present in the operating theater. The primary physician typically operates an interventional medical device using both hands and therefore has to either put down the medical device or request another person of the medical staff to operate the systems for her or him.

For example, in a surgical intervention called transseptal puncture of the heart, an elongated medical device in form of a catheter, after having been inserted into either a femoral or brachiocephalic vein, respectively, is advanced through the blood vessels until the catheter tip reaches the correct place for the puncture. An event to be triggered in the medical system is then to tag a landmark at the position of the tip of the catheter so that a transseptal needle can then be brought through the catheter and aligned with the targeted landmark. In order to tag the landmark, the primary physician maneuvering the catheter has to either put down the catheter or request another person in the operating theater to trigger the tagging of the landmark.

When using an elongated interventional medical device like catheter or guide wire, optical shape sensing is a useful technology to reconstruct a three-dimensional shape of the medical device, in particular of that section of the medical device which is inserted into the patient's body and thus cannot be viewed with the physician's eyes. With optical shape sensing using an optical shape sensing fiber integrated in the interventional medical device, the three-dimensional shape of the medical device can be known and thus be made "visible" up to the tip of the device. Optical shape sensing fibers can be integrated into a wide range of medical devices to provide live guidance or navigation of medical procedures. In vascular navigation, it is typical for the physician or user to position targets or rings at important positions during a procedure. These can serve as notable points to be returned to at various stages of the procedure. In the shape-sensed catheter or guide wire, these target shapes or points may be stored when triggered by the user. At present, the acquisition of relevant positions within the patient's body is performed with a mouse click, which, however, requires the use of two hands or two operators, neither of which is ideal for workflow.

WO 2013/168056 A1 discloses devices, systems and methods for detecting gestures. The devices, systems and methods use optically shape sensing devices for gesture controlling systems for use in health care institutions.

US 2014/0357988 A1 discloses a sensor device for detecting a dose of radiation received at the sensor device. The sensor device comprises a flexible body having a cross-section being comparatively small relative to the length of the device, cladding at the flexible body, the cladding converting incoming radiation into visible light, and an optical shape sensing device disposed within the flexible body and configured to determine a shape of the flexible instrument relative to a reference, the shape sensing device configured to collect information based on its configuration to map an intraluminal structure during a procedure.

SUMMARY OF THE INVENTION

It is an object of the present invention to provide a medical system which enables triggering events in the medical system without the need of operating additional devices other than the interventional medical device held in hand by the user.

It is a further object of the present invention to achieve the afore-mentioned object with a minimum of structural expenditure of the medical system.

In a first aspect of the present invention, a medical system for using an interventional elongated medical device having an optical fiber configured for optical shape sensing of the medical device is provided, the system comprising:
  a detection unit configured to detect a confined manipulation section along the medical device for manipulation by a user without an interaction interface arranged on the medical device; and
  an analysis unit configured to analyze a user manipulation applied to the manipulation section based on optical shape sensing of the medical device in the manipulation section and to trigger an event in the medical system, if the analysis unit identifies the user manipulation in the manipulation section as a specific manipulation associated with the event to be triggered.

According to the present invention, the interventional elongated medical device, for example a catheter or guide wire equipped with an optical shape sensing fiber can also be used for controlling or operating other devices, parts or sub-systems of the medical system. Thus, the user of the interventional elongated medical device does not have to put down the interventional medical device and does not have to request another person in the operating theater to control or operate the devices, parts or sub-systems, but the user of the interventional medical device him- or herself can perform these controls or operations by simply manipulating the medical device in the confined manipulation section of the medical device. The work-flow of a surgical intervention is improved thereby.

When maneuvering an interventional elongated medical device like a catheter, guidewire or endoscope, only a small number of degrees of freedom of manipulation are used, which usually are limited to advancing the interventional medical device or pulling it back in longitudinal direction or to rotate the interventional medical device about its longitudinal axis. Thus, a number of degrees of freedom of manipulation different from the afore-mentioned ones are available as control manipulations, which can be applied to the medical device in order to trigger an event in the medical system, for example to tag one or more landmarks during navigation of the medical device or to operate other devices or sub-systems.

The present invention renders it possible to make use of these additional degrees of freedom of manipulation of the interventional medical device for triggering an event in the medical system. However, in order to simplify the recognition of trigger manipulations in terms of calculating time, only manipulations in a confined manipulation section of the medical device are queried by the system. The manipulation section does not require an interaction interface like a hub, a switch, control knob or the like. This means that the trigger manipulations are directly applied to the outer wall (shaft) of the medical device. Thus, the structural expenditure of the medical system is very low.

In order to detect the confined manipulation section along the medical device, the medical system comprises a detection unit configured to detect the confined manipulation section along the medical device.

The detection unit can be configured in different ways in order to detect the confined manipulation section along the medical device, as will be explained below.

Further, the medical system comprises an analysis unit. The analysis unit is configured to analyze a user manipulation applied to the manipulation section. The analysis is based on optical shape sensing of the medical device in the manipulation section. If the user applies a specific manipulation to the manipulation section, the analysis unit identifies this specific manipulation as a control manipulation and triggers the event associated with the specific manipulation.

Specific manipulations which can be applied to the medical device will be explained below.

Preferred embodiments of the invention are defined in the dependent claims.

Preferably, the detection unit is configured to detect the manipulation section based on optical shape sensing of the medical device. This has the advantage that no further external means are required in order to detect the confined manipulation section along the medical device, but the detection unit simply uses the optical shape sensing infrastructure of the medical system.

Further, it is preferred if the detection unit is configured to detect the manipulation section based on the specific manipulation applied to the medical device. This embodiment is particularly advantageous because the detection unit and the analysis unit can be realized as a single unit, for example implemented as software in the optical shape sensing system of the medical system.

In other embodiments, the detection unit is configured to detect the manipulation section based on external tracking of the manipulation section, e.g. by external radiation.

The afore-mentioned embodiments of the detection unit can be at least partly based on the optical shape sensing infrastructure of the medical system, and some embodiments are based on external detection mechanisms like the external tracking via radiation.

The specific manipulation associated with the event to be triggered can consist of or comprise the following preferred embodiments.

In general, the specific manipulation advantageously is a manipulation different from displacing the medical device in or transverse to the direction of a longitudinal axis of the medical device and different from rotating the medical device about the longitudinal axis of the medical device. In this way, the specific manipulation used for triggering an event can be surely distinguished by the analysis unit from manipulations which are typical for maneuvering the interventional medical device during an intervention, like advancing, pulling back, lateral displacement, or rotating the medical device.

In a further preferred embodiment, the specific manipulation is a time-based pattern of a sequence of manipulations over time. The manipulations can be of the same type, but can also be of a different type. A time-based pattern of a sequence of manipulations over time has the advantage of further enhancing the differentiation of the specific manipulation from manipulations which are used for maneuvering the interventional medical device in an intervention.

Further preferably, the specific manipulation is at least one deformation of the medical device into a specific shape. Examples of such specific shapes are an S-shape, a full loop or half-loop, an out of plane half-loop, and the like.

Further preferably, the specific manipulation is at least one pinch of the medical device. Such a manipulation can be applied very simply by the user merely using the thumb and the index finger of the same hand.

Further preferably, the specific manipulation is at least one pinch or deformation of the medical device, followed by a stroke, and then a release of the pinch or deformation. In this way, the pinch or deformation can be used as the starting point of an event, while the event is maintained during the stroke, e.g. a pull back of the medical device, and the release of the pinch or deformation can be used as the end point of the event. An advantageous example of use of this embodiment is a length measurement, for example of the length of a vessel, from the beginning of the pinch or deformation at a first position to the release of the pinch or deformation at a second position, wherein the measured length is the length of the stroke.

Further preferably, the specific manipulation is at least one tap onto the medical device, or a sequence of taps according to a specific frequency or rhythm. A tap or a plurality of taps can also be very easily applied to the medical device by a finger of the user.

Further preferably, the specific manipulation is a torque or tension build-up in the medical device. Further preferably, the specific manipulation can also be recognized by calculating the direction vector between the beginning and the end of the manipulation section given by the relative hand position direction.

Further preferably, the specific manipulation comprises a sequence of equal or different single manipulations over time. For example, the specific manipulation can be a sequence of a deformation of the medical device into a specific shape and at least one pinch, and/or at least one tap onto the medical device.

Preferably, the elongated medical device is a catheter, guide wire or endoscope.

It is to be understood that the above-described embodiments can be used in combinations without departing from the scope of the present invention.

In a second aspect of the present invention, a method for triggering an event in a medical system is provided, the system using an interventional elongated medical device having an optical fiber configured for optical shape sensing of the medical device; the method comprising:

detecting a confined manipulation section along the medical device configured for manipulation by a user without an interaction interface arranged on the medical device, analyzing a user manipulation applied to the manipulation section based on optical shape sensing of the medical device in the manipulation section, and triggering the event, if the user manipulation in the manipulation section has been identified as a specific manipulation associated with the event to be triggered.

The method according to the invention has similar and/or identical advantages as the medical system according to the invention, and it is to be understood that the method according to the invention has similar and/or identical preferred embodiments as the medical system according to the invention and as defined in the dependent claims.

According to a third aspect of the present invention, a computer program is provided comprising program code means for causing a computer to carry out the steps of the method according to the second aspect when said computer program is carried out on a computer.

BRIEF DESCRIPTION OF THE DRAWINGS

These and other aspects of the invention will be apparent from and elucidated with reference to the embodiments described hereinafter. In the following drawings

DETAILED DESCRIPTION OF THE INVENTION

Figure 1:
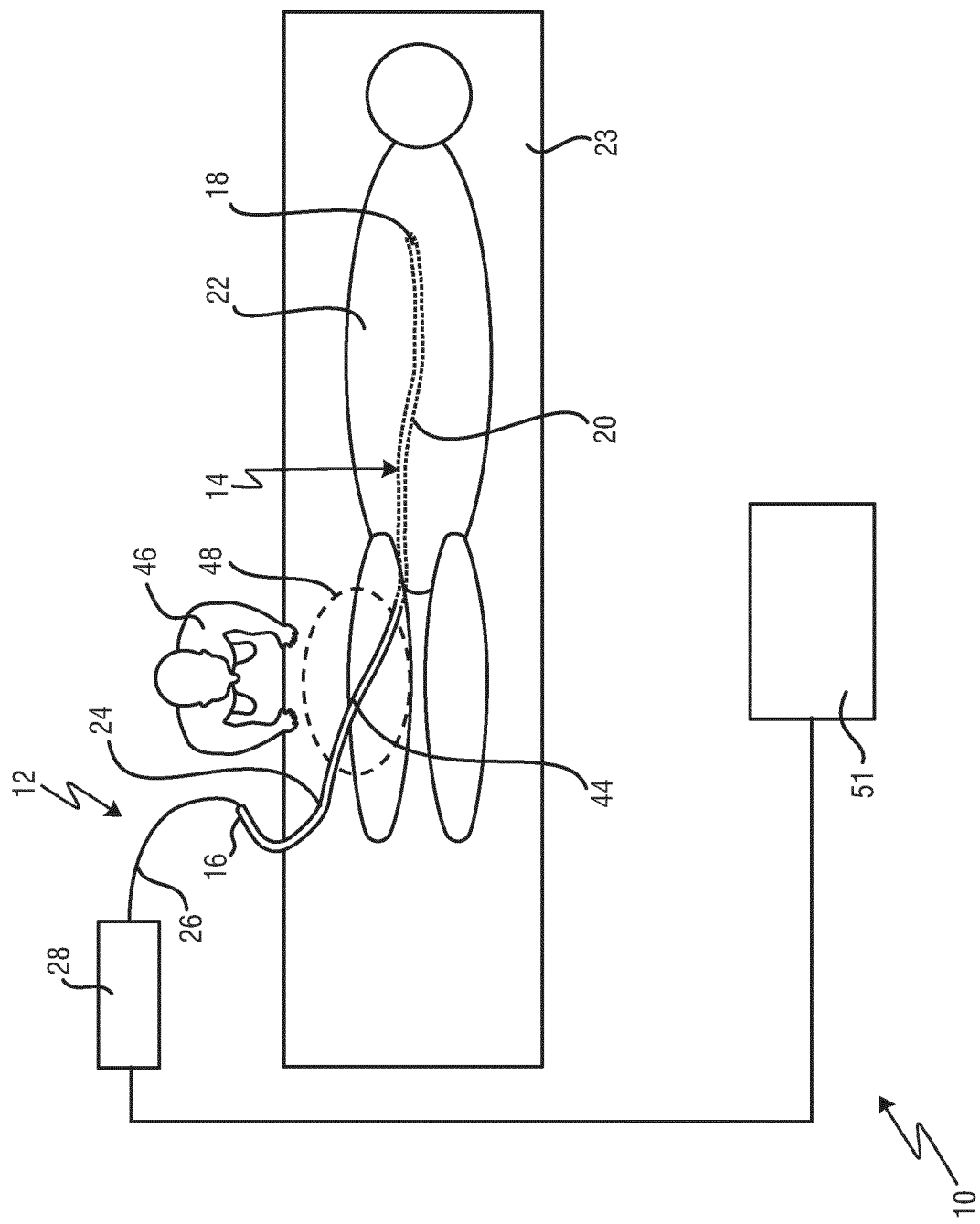
FIG. 1 shows a medical system during use in a surgical intervention.

FIG. 1 shows a medical system labeled in total with reference numeral 10 in use in a surgical intervention. Examples for such surgical interventions will be described later.

The medical system 10 comprises an optical shape sensing unit 12. The optical shape sensing unit 12 is configured to cooperate with a shape sensed interventional elongated medical device 14 that is used by and connected to the system. In some embodiments of the system 10, the optical shape sensing unit 12 comprises the shape sensed interventional elongated medical device 14. The medical device 14 can be a catheter, a guide wire or a flexible endoscope. The medical device 14 has a proximal end 16 and a distal end or tip 18. A section 20 of the medical device 14 is shown inserted into the body of a patient 22 lying on an operating table 23. The section 20 of the medical device 14 which is inserted into the body 22 is shown in broken lines. The section 20 can also be referred to as the navigation section of the medical device 14. A section 24 of the medical device 14 which is outside the body 22 of the patient, is shown in solid lines.

The optical shape sensing unit 12 is further configured to cooperate with an optical fiber 26 configured for optical shape sensing of the medical device 14.

The optical fiber 26 is shown in FIG. 1 starting from an optical shape sensing console 28 and extending through the interior of the medical device 14 up to the distal end 18 of the medical device 14.

Before continuing the description of FIG. 1, the principle set-up and function of the optical shape sensing unit 12 will be described with reference to FIG. 2.

Figure 2:
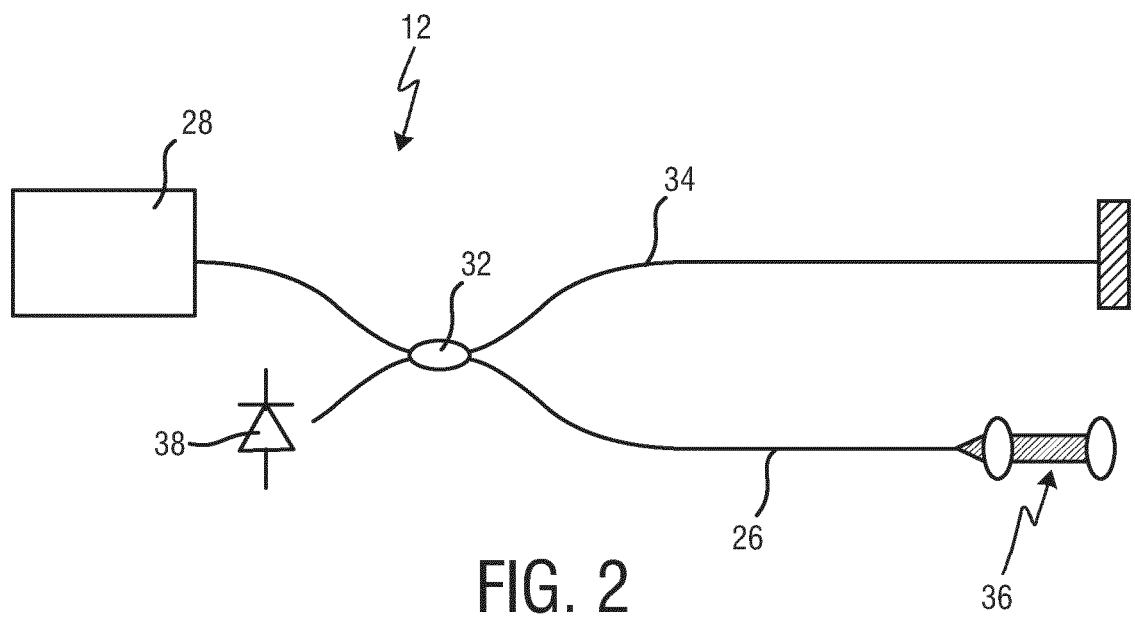
FIG. 2 shows an optical shape sensing system which can be used in the medical system in FIG. 1.

FIG. 2 schematically shows a possible configuration of optical shape sensing using the optical fiber 26, wherein the medical device 14 is not shown in FIG. 2.

In practice, the optical fiber 26 may be any type of optical fiber suitable for optically sensing the medical device 14. Examples of the optical fiber 26 include, but are not limited to, a flexible optically transparent glass or plastic fiber incorporating an array of fiber Bragg gratings integrated along a length of a fiber as known in the art, and a flexible optically transparent glass or plastic fiber having naturally variations in its optic refractive index occurring along a length of the fiber as known in the art (e.g., a Rayleigh scattering based optical fiber). The optical fiber 26 may be a single core fiber or, preferably, a multi-core fiber.

The optical shape sensing unit 12 can be based on optical frequency domain reflectometry using a tunable light source which may be arranged in the console 30. The output of the light source travels through a splitter 32 which directs a part of the signal into a reference arm fiber 34 and the remaining part of the signal into the optical fiber 26 forming the sample arm of the fiber-optic interferometer. The optical fiber 26 illuminates and receives the light reflected at an interrogated area 36. The interrogated area 36, in the present example, can be the area of the optical fiber 26 within the medical device 14 between the distal end 18 and the proximal end 16.

The interference between the signal returned from the reference arm fiber 34 and the signal returned from the sample arm optical fiber 26 is detected with a photodetector 38, while the wavelength of the monochromatic source is swept and the path length of the reference and sample arm are held constant. The axial reflectivity profile is obtained by discrete Fourier transform of the sampled detector signals.

In practice, the optical shape sensing console 28 may be any device of the system structurally configured for transmitting light to the optical fibers 34 and 26 and receiving reflected light from the optical fibers 34 and 26. The optical shape sensing console 28 may employ an optical Fourier domain reflectometer and other appropriate electronics/devices/software for reconstructing the 3D shape of the fiber 26 along the length thereof from the reflection spectrum received by the detector 38.

Figure 2A:
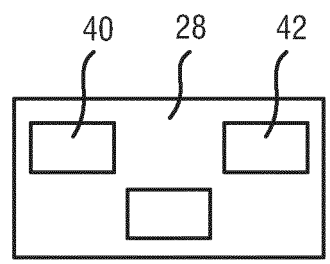
FIG. 2A shows a part of the optical shape sensing system in FIG. 2.

With reference to FIG. 1 again, and also with reference to FIG. 2A, the medical system 10 comprises a detection unit 40 and an analysis unit 42 which may be, as shown in FIG. 2A, integrated into the optical shape sensing console 28. The detection unit 40 and the analysis unit 42 can be realized in form of software, but also as hardware devices. The detection unit 40 and the analysis unit 42 can also be configured as one single unit in form of software or hardware.

The detection unit 40 is configured to detect a confined manipulation section 44 along the medical device 14 which can be manipulated by a user 46, for example a physician during a surgical procedure. In FIG. 1, the manipulation section 44 is indicated by a broken line 48. The manipulation section 44 is a length of the medical device 14, which is outside the body 22 of the patient. In particular, the manipulation section does not require an interaction interface like a hub, control knob or the like arranged on the medical device 14, but the manipulation section is manipulated by the user 46 for triggering an event simply by using his or her hands holding the medical device 14.

The analysis unit 42 is configured to analyze manipulations applied by the user 46 to the manipulation section 44. The analysis is based on optical shape sensing of the medical device 14 in the manipulation section 44. In case the analysis unit 42 identifies the user manipulation applied to the manipulation section 44 as a specific manipulation, embodiments of which will be described below, the analysis unit 42 triggers an event in the medical system 10. Such an event may be the transmittal of a control signal to a controller 51 of the medical system 10, which, for example, controls a specific operation of the medical system 10.

It may be conceived that different specific manipulations can be associated with different events to be triggered.

Further, the specific manipulation or specific manipulations carried out by the user are directly applied to the medical device (14) without an interface like a control knob or hub, but simply by acting on the manipulation section 44 when the manipulation section 44 is gripped by the user's hand or hands.

Since there is no interface arranged on the medical device 14 in the manipulation section 44, the analysis unit has to "know", where along the medical device 14 it has to look for a specific manipulation. Therefore, the detection unit 40 is provided to recognize or detect the manipulation section 44 along the medical device 14.

There are several ways how the detection unit can be configured for detecting the confined manipulation section 44.

A preferred way is that the detection unit 40 is configured to detect the manipulation section 44 based on optical shape sensing of the medical device 14. It is particularly preferred if the detection unit is configured to detect the manipulation section based on the specific manipulation applied to the medical device 14.

In this way, detection of the manipulation section 44 as well as analyzing the specific manipulation applied to the medical device 14 can be performed based on the same technology.

The insight behind this embodiment is that when the user 46 maneuvers the interventional medical device 14, there are usually only a limited number of degrees of freedom used for maneuvering the medical device 14. Typically, the user 46 advances the medical device 14 in longitudinal direction in order to place the distal end 18 at a target site in the body 22, pulls back the medical device 14 in longitudinal direction of the medical device 14, laterally displaces the medical device, and/or rotates the medical device 14 about its longitudinal axis. Thus, a larger number of degrees of freedom of manipulation remain unused during "normal" operation/navigation of the medical device 14. These remaining degrees of freedom can be advantageously used as specific manipulations for triggering events in the medical system 10.

Principally, a specific manipulation for triggering an event can be any manipulation different from displacing the medical device 14 in or transverse to the direction of the longitudinal axis of the medical device 14 and different from rotating the medical device about its longitudinal axis, and which is detectable by optical shape sensing.

FIGS. 3 to 9 show embodiments of specific manipulations which are different from merely displacing the medical device 14 and from rotating the medical device 14 about the longitudinal axis thereof. FIGS. 3 to 9 show the medical device 14 in the area of the manipulation section 44 with the optical fiber 26 inserted therein.

Figure 3:
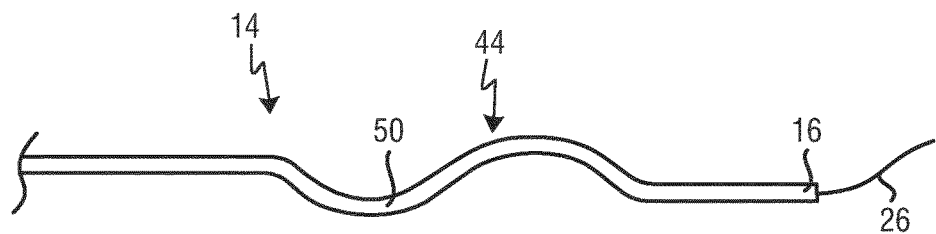
FIG. 3 shows an embodiment of a specific manipulation applied to an interventional medical device used in the medical system in FIG. 1.
Figure 4:
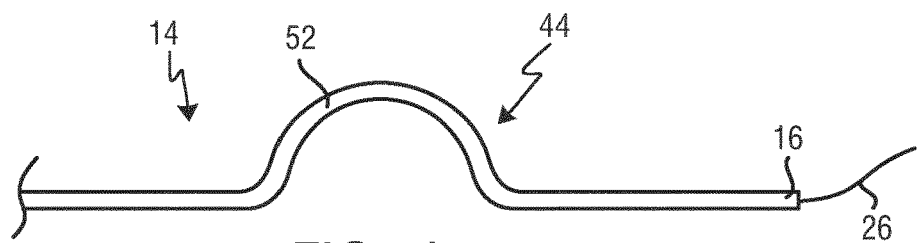
FIG. 4 shows a further embodiment of a specific manipulation applied to the medical device.
Figure 5:
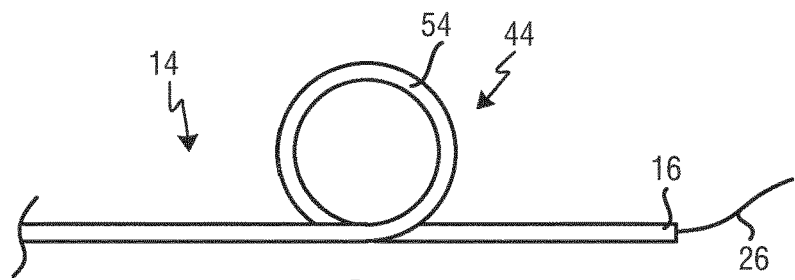
FIG. 5 shows a further embodiment of a specific manipulation applied to the medical device.

Specifically, FIGS. 3 to 5 show embodiments of specific manipulations which are a deformation of the medical device 14 into a specific shape. FIG. 3 shows an S-shape 50 applied to the medical device 14. FIG. 4 shows a half-loop 52 applied to the medical device 14. FIG. 5 shows a full loop 54 applied to the medical device 14. The S-shape 50, the half-loop 52, and/or the full loop 54 can be in-plane or out of plane, wherein the plane for example here is the plane of the drawings.

Figure 6:
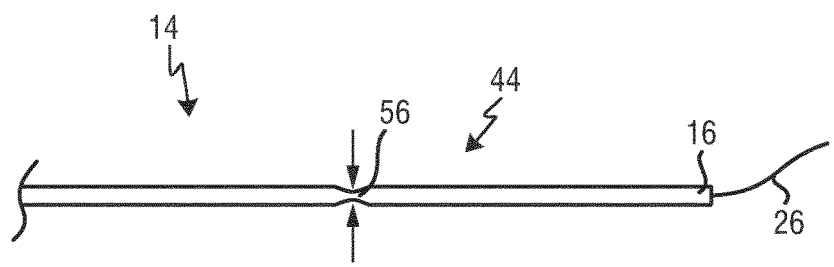
FIG. 6 shows a further embodiment of a specific manipulation applied to the medical device.

FIG. 6 shows a specific manipulation applied to the medical device 14 which is a pinch 56 of the medical device 14. The pinch 56 can be applied by simply using the thumb and the index finger of one hand. Like the specific manipulations shown in FIGS. 3 to 5 which consist in specific deformations of the medical device and, thus, of the optical fiber 26 inserted in the medical device 14, the pinch 56 also causes strain in the optical fiber 26 leading to a corresponding optical shape sensing signal detected by the shape sensing console 28.

Figure 7:
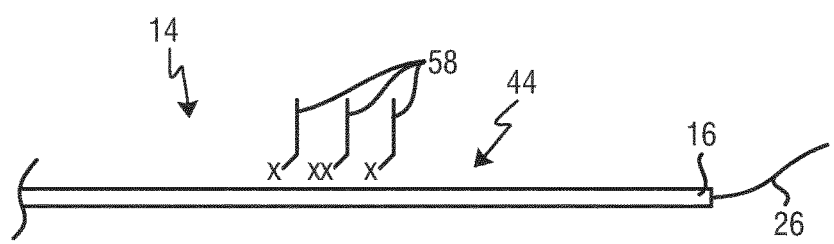
FIG. 7 shows a further embodiment of a specific manipulation applied to the medical device.

FIG. 7 shows a further embodiment of a specific manipulation of the medical device 14 which is a sequence of taps 58 applied onto the medical device 14 according to a specific frequency or rhythm.

The taps 58 can be applied to medical device 14 by tapping with one or more fingers onto the medical device 14.

The sequence of taps 58 is an embodiment of a more general type of specific manipulations, which in general are a time-based pattern of a sequence of manipulations over time. It is conceivable that such a time-based pattern of a sequence of manipulations over time cannot only be in form of taps, but can also be embodied as a sequence of deformations such as shown in FIGS. 3 to 5, a sequence of pinches as shown in FIG. 6, a combination of deformations, pinches, and/or taps.

It is also conceivable that the specific manipulation applied to the medical device 14 can comprise a sequence of equal or different single manipulations over time, for example a sequence of single manipulations like those shown in FIGS. 3 to 7.

Figure 8A:
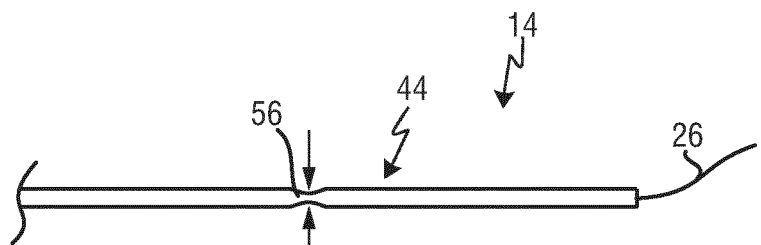
FIGS. 8A-C show a further embodiment of a specific manipulation applied to the medical device.
Figure 8B:
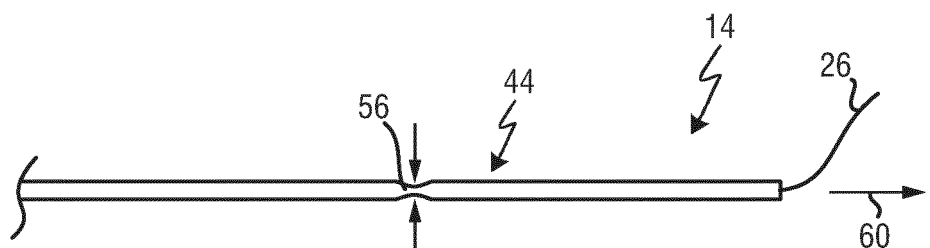
Figure 8C:
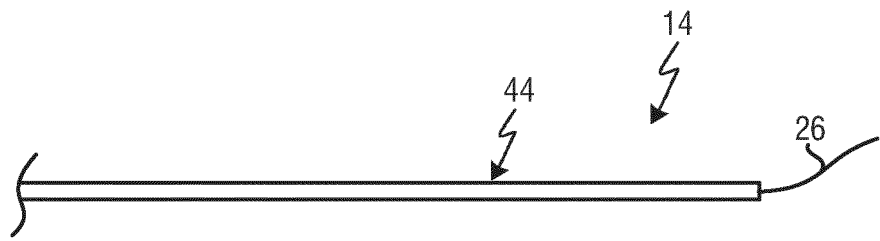

Another embodiment of a specific manipulation in form of a time-based pattern of a sequence of manipulations over time is shown in FIGS. 8A to 8C. FIG. 8A shows a specific manipulation in form of the pinch 56 as already described with respect to FIG. 6. Then, a stroke according to an arrow 60 is applied to the medical device, which here consists in pulling back the medical device, while the pinch 56 is maintained. The pinch 56 as well as the stroke 60 can be applied to the medical device 14 by the same hand. According to FIG. 8C, after a certain stroke of, for example, a few centimeters, the pinch 56 is released. A specific manipulation as shown in FIGS. 8A to 8C can be advantageously used for a length measurement within the patient's body from the beginning of the pinch 56 to the release of the pinch 56, wherein the measured length is the length of the stroke.

Figure 9:
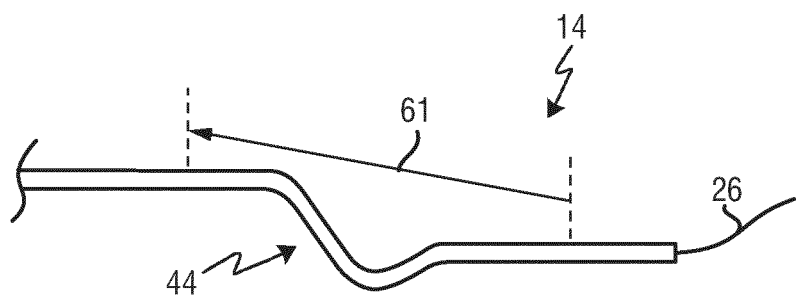
FIG. 9 shows a still further embodiment of a specific manipulation applied to the medical device.

FIG. 9 shows another embodiment of a specific manipulation applied to the medical device 14 which consists in building up a torque or tension in the medical device 14. Further, as shown in FIG. 9, a direction vector 61 can be calculated between begin and end of the manipulation section 44 and the calculated direction vector is a measure of the relative hand orientation, which can be used to trigger an event.

Figure 10:
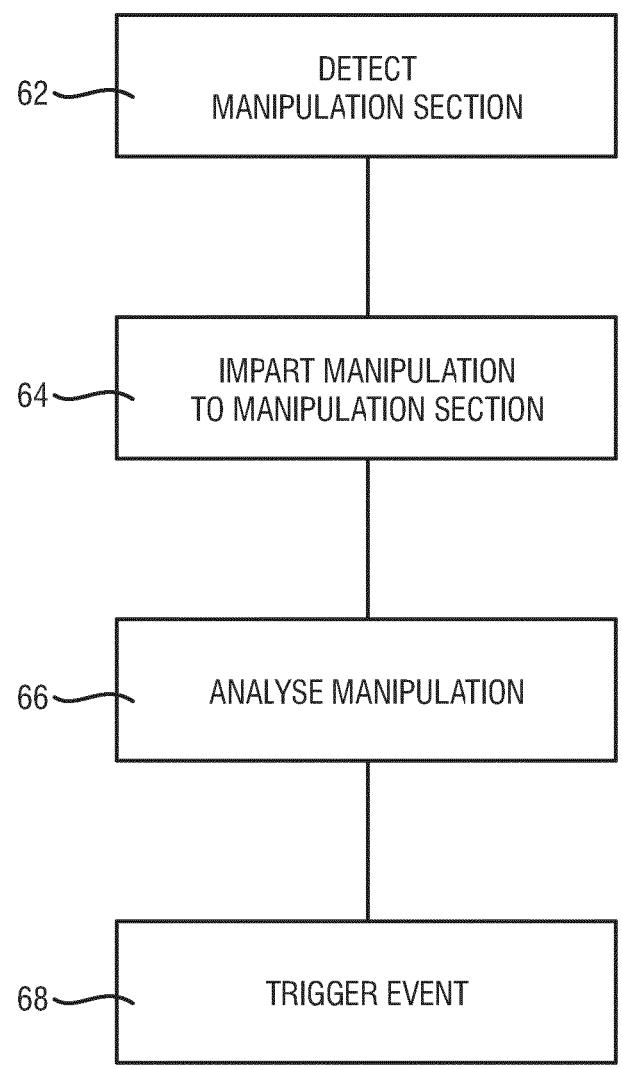
FIG. 10 shows a flow diagram of a method for triggering an event.

While it is preferred that the detection unit 40 detects the manipulation section 44 based on the occurrence of a specific manipulation like those which have been described above with respect to FIGS. 3 to 9, it is also conceivable that the detection unit 40 is configured to detect the manipulation section 44 in a different way, for example using external tracking means like radiation FIG. 10 shows a flow diagram of a method for triggering an event in a medical system like the medical system 10 in FIG. 1 that uses the interventional elongated medical device 14 equipped with an optical fiber 26 configured for optical shape sensing of the medical device 14.

The method comprises a step 62 according to which the confined manipulation section 44 is detected along the medical device 14, wherein the manipulation section is configured for manipulation by the user without an interaction interface arranged on the medical device 14.

In step 64, a manipulation is applied by the user 46 on the medical device 14. In particular, the manipulation applied can be one or more of the above-described specific manipulations (FIGS. 3 to 9).

In step 66, the user manipulation applied to the manipulation section 44 according to step 64 is analyzed based on optical shape sensing of the medical device 14 in the manipulation section 44.

In step 68, the event is triggered, if the user manipulation according to step 64 in the manipulation section 44 has been identified as a specific manipulation associated with the event to be triggered.

In case that the step of detecting the manipulation section 44 according to step 62 is based on the detection of a specific manipulation applied to the medical device 14, step 44 is performed prior to step 62 so that in this case the order of the method steps is 64-62-66-68.

In the following, some examples of use of the medical system 10 and the before-mentioned method are described.

For example, the medical system 10 in FIG. 1 is used in a surgical procedure called transseptal puncture of the heart of the patient. In this case, the medical device 14 in form of a catheter equipped with the optical fiber 26 configured for optical shape sensing is introduced through the femoral vein and advanced until the distal end or tip 18 of the medical device 14 is positioned at the correct place for performing the puncture of the heart. When the distal end 18 of the medical device 14 is positioned correctly, the user 46 applies a specific manipulation to the medical device 14, for example the user double-taps onto the medical device 14. The detection unit 40 detects the manipulation section 44 based on this double tap, and the analyzing unit 42 identifies the double tap as a specific manipulation and triggers an associated event, for example tagging a landmark at the position of the distal end 18 of the medical device 14. Now, a transseptal needle can be brought through the medical device 14 and aligned with the targeted landmark.

Another example similar to the afore-mentioned example is marking an ablation point during an atrial fibrillation (electrophysiology) intervention, where the user can easily mark ablation points on the anatomy using the system 10 and method described herein.

Another example is the use of the medical system 10 in a surgical procedure called intravascular ultrasound (IVUS) diagnosis. In this case, the medical device 14 is an IVUS catheter equipped with an ultrasound probe at the distal tip into which a guide wire equipped with the optical fiber 26 is inserted for navigating the IVUS catheter 14 through the blood vessel. In the IVUS procedure, the physician 46 wants to collect a series of ultrasound and optical shape sensing data points during a pullback of the IVUS catheter 14. Before beginning of the pullback, the user 46 applies a small bent or a pinch to the medical device 14. The user 46 holds that small bent or the pinch during the pullback of the device 14 until the end of the pullback, at which time the user releases the small bent or the pinch. The detection unit 40 detects the manipulation section 44 via the small bent or the pinch. The analysis unit 42 recognizes the small bent or the pinch in the manipulation section 44 as a specific manipulation to trigger the event, namely to acquire the ultrasound and optical shape sensing data points during the pullback of the medical device 14.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

The computer program which also is part of the invention, may be stored/distributed on a suitable medium, such as an optical storage medium or a solid-state medium supplied together with or as part of other hardware, but may also be distributed in other forms, such as via the Internet or other wired or wireless telecommunication systems.

Any reference signs in the claims should not be construed as limiting the scope.

The invention claimed is:

1. A medical system for using an interventional elongated medical device having an optical fiber configured for optical shape sensing of the medical device, the medical system comprising:
   a computer; and
   a non-transitory storage medium for storing instructions that, when executed by the computer, cause the computer to:
   detect a confined manipulation section of the medical device, the confined manipulation section being a length of the medical device configured to be gripped by a user for maneuvering the medical device inside a body and for applying a user manipulation to the confined manipulation section, the user manipulation comprising at least one of a pinch into an outer wall of the medical device or a deformation of the confined manipulation section into a predefined shape, while the user grips the confined manipulation section; and
   analyze the user manipulation applied to the confined manipulation section based on optical shape sensing of the medical device in the confined manipulation section, and to trigger an event to be carried out at a distal portion of the medical system in response to identifying the user manipulation as being associated with the event to be triggered.

2. The medical system of claim 1, wherein the user manipulation is different from displacing the medical device in or transverse to a direction of a longitudinal axis of the medical device and from rotating the medical device about the longitudinal axis of the medical device.

3. The medical system of claim 1, wherein the user manipulation comprises a pattern of a sequence of manipulations over time.

4. The medical system of claim 1, wherein the at least one of the pinch or the deformation of the confined manipulation section is followed by a stroke of the medical device, and then a release of the at least one of the pinch or the deformation.

5. The medical system of claim 1, wherein the user manipulation further comprises a tap or a sequence of taps onto the medical device according to a specific frequency or rhythm.

6. The medical system of claim 1, wherein the user manipulation further comprises a torque or tension build-up in the medical device.

7. The medical system of claim 1, wherein the user manipulation further comprises a sequence of equal or different single manipulations over time.

8. The medical system of claim 1, wherein the elongated medical device is a catheter, a guidewire, or an endoscope.

9. The medical system of claim 1, wherein the predefined shape into which the confined manipulation section is deformed comprises an S-shape, a half-loop, or a full loop.

10. A method for triggering an event in a medical system using an interventional elongated medical device having an optical fiber configured for optical shape sensing of the medical device; the method comprising:
    detecting a confined manipulation section of the medical device, the confined manipulation section being a length of the medical device configured to be gripped by a user for maneuvering the medical device inside a body and for applying a user manipulation to the confined manipulation section, the user manipulation comprising at least one of a pinch into an outer wall of the medical device or a deformation of the confined manipulation section into a predefined shape, while the user grips the confined manipulation section;
    analyzing the user manipulation applied to the confined manipulation section based on optical shape sensing of the medical device in the confined manipulation section; and
    triggering the event in response to identifying the user manipulation in the confined manipulation section as being associated with the event to be triggered, the event to be performed at a distal portion of the medical device.

11. The method of claim 10, wherein the user manipulation excludes displacing the medical device in or transverse to a direction of a longitudinal axis of the medical device and from rotating the medical device about the longitudinal axis of the medical device.

12. The method of claim 10, wherein the user manipulation comprises a pattern of a sequence of manipulations over time.

13. The method of claim 10, wherein the at least one of the pinch or the deformation of the confined manipulation section is followed by a stroke of the medical device, and then a release of the at least one of the pinch or the deformation.

14. The method of claim 10, wherein the user manipulation further comprises a tap or a sequence of taps onto the outer wall of the medical device according to a specific frequency or rhythm.

15. The method of claim 10, wherein the user manipulation further comprises a torque or tension build-up in the medical device.

16. The method of claim 10, wherein the user manipulation further comprises a sequence of equal or different single manipulations over time.

17. The method of claim 10, wherein the predefined shape into which the confined manipulation section is deformed comprises an S-shape, a half-loop, or a full loop.

18. A non-transitory computer readable medium comprising computer program instructions that, when executed by a computer, cause the computer to:
    detect a confined manipulation section of medical device, the confined manipulation section being a length of the medical device configured to be gripped by a user for maneuvering the medical device inside a body and for applying a user manipulation to the confined manipulation section, wherein the user manipulation comprises at least one of a pinch into an outer wall of the medical device or a deformation of the confined manipulation section into a predefined shape, while the user grips the confined manipulation section;
    analyze the user manipulation applied to the confined manipulation section based on optical shape sensing of the medical device in the confined manipulation section; and
    trigger an event in response to identifying the user manipulation in the confined manipulation section as being associated with the event to be triggered, wherein the event is to be performed at a distal portion of the medical device.

19. The non-transitory computer readable medium of claim 18, wherein the predefined shape into which the confined manipulation section is deformed comprises an S-shape, a half-loop, or a full loop.

20. The non-transitory computer readable medium of claim 18, wherein the at least one of the pinch or the deformation of the confined manipulation section is followed by a stroke of the medical device, and then a release of the at least one of the pinch or the deformation.

* * * * *